(12) United States Patent
Benedict

(10) Patent No.: US 11,723,741 B1
(45) Date of Patent: Aug. 15, 2023

(54) CONTAINER FOR HOLDING AND DISPENSING MEDICAL GLOVES OR OTHER CONSUMABLES

(71) Applicant: Mark Benedict, Pembroke Pines, FL (US)

(72) Inventor: Mark Benedict, Pembroke Pines, FL (US)

( * ) Notice: Subject to any disclaimer, the term of this patent is extended or adjusted under 35 U.S.C. 154(b) by 0 days.

(21) Appl. No.: 17/074,148

(22) Filed: Oct. 19, 2020

Related U.S. Application Data

(60) Provisional application No. 62/923,339, filed on Oct. 18, 2019.

(51) Int. Cl.
*A61B 42/40* (2016.01)

(52) U.S. Cl.
CPC .................... *A61B 42/40* (2016.02)

(58) Field of Classification Search
CPC .......... A47K 10/421; A47K 2010/3233; A47K 2010/3266; A47K 5/1204; B65D 83/0817; B67D 5/06; A61B 42/40
USPC ........ 221/45, 276, 33; 664/179; 222/153.03; 220/478, 477
See application file for complete search history.

(56) References Cited

U.S. PATENT DOCUMENTS

| | | | | |
|---|---|---|---|---|
| 1,622,597 A | * | 3/1927 | Mangold | A47F 1/085 |
| | | | | 312/249.7 |
| 1,689,571 A | * | 10/1928 | West | A47K 10/422 |
| | | | | 221/45 |
| 2,081,564 A | * | 5/1937 | Tuszynski | A47K 10/424 |
| | | | | D7/631 |
| 3,223,281 A | * | 12/1965 | Larkin | A47K 10/185 |
| | | | | 221/61 |
| 3,425,595 A | * | 2/1969 | Shapira | A47K 10/422 |
| | | | | 221/62 |
| 3,589,555 A | * | 6/1971 | Burkhalter, Jr. | A47K 10/427 |
| | | | | 221/45 |
| 3,982,659 A | * | 9/1976 | Ross | B65D 83/0805 |
| | | | | 225/106 |
| 4,535,912 A | * | 8/1985 | Bonk | A47K 10/3809 |
| | | | | 225/106 |

(Continued)

FOREIGN PATENT DOCUMENTS

| | | | | |
|---|---|---|---|---|
| GB | 2355178 A | * | 4/2001 | ............... A47F 1/08 |
| GB | 2528242 | | 1/2016 | |

(Continued)

*Primary Examiner* — Rakesh Kumar
(74) *Attorney, Agent, or Firm* — John Rizvi, The Patent Professor, P.A.

(57) ABSTRACT

A container is provided for receipt of boxes of medical gloves or other consumables. The container includes a box holder having a dispensing opening in a front panel of the box holder and a movable cover or tray which can be moved from a first or undeployed condition to a second or deployed condition in which the movable cover or tray extends outwardly from a front panel of the box holder and can catch any medical gloves fallen from the boxes before they land on the ground and are contaminated. The movable panel may be pivotally mounted to and/or extendable from the box holder. When pivotally mounted to the box holder, the movable panel covers the dispending opening in the front panel and protects the medical gloves from dust and other contaminants when the movable panel is in the first or undeployed condition.

13 Claims, 13 Drawing Sheets

(56) References Cited

U.S. PATENT DOCUMENTS

| | | | |
|---|---|---|---|
| 4,953,747 A * | 9/1990 | Wenkman | A47K 10/427 221/56 |
| 4,997,105 A | 3/1991 | Fischer | |
| 5,570,808 A | 11/1996 | Tassoni | |
| 5,894,931 A * | 4/1999 | Dunn | A47F 3/145 312/50 |
| 5,996,841 A * | 12/1999 | Marrocco | G07F 11/04 221/268 |
| 6,062,421 A | 5/2000 | Marley | |
| 6,257,443 B1 * | 7/2001 | LaCount | A47K 10/427 221/58 |
| 6,651,827 B1 * | 11/2003 | Eberwein | A47F 1/126 206/215 |
| 6,669,157 B1 | 12/2003 | Willin et al. | |
| 6,708,841 B2 | 3/2004 | Baughman | |
| 6,820,753 B2 * | 11/2004 | Kurtz | A47K 10/20 211/49.1 |
| 6,959,891 B2 * | 11/2005 | Kapiloff | A47K 10/3836 242/597.5 |
| 8,196,775 B1 | 6/2012 | Ballesteros | |
| 8,887,960 B2 * | 11/2014 | Hardman | B67D 7/02 222/165 |
| 9,579,155 B2 | 2/2017 | Cosentino, II | |
| D783,304 S | 4/2017 | Gray et al. | |
| 9,624,027 B2 * | 4/2017 | DeGraaf | B65D 25/005 |
| 9,682,390 B2 * | 6/2017 | Ophardt | A47K 5/12 |
| D809,318 S | 2/2018 | Hammons et al. | |
| 10,220,979 B2 | 3/2019 | Silkaitis | |
| 10,478,023 B2 * | 11/2019 | Osborne, Jr. | B65H 1/00 |
| 10,980,377 B1 * | 4/2021 | Falk | A47K 10/422 |
| 2003/0015543 A1 * | 1/2003 | Turbett | A47K 10/424 221/63 |
| 2003/0106867 A1 * | 6/2003 | Caterinacci | A47F 1/126 211/59.3 |
| 2004/0099623 A1 * | 5/2004 | Kurtz | A47K 10/20 248/905 |
| 2005/0000975 A1 | 1/2005 | Carco et al. | |
| 2005/0279757 A1 * | 12/2005 | Bitowft | A47K 10/426 221/45 |
| 2006/0086748 A1 * | 4/2006 | Burns | A47K 10/426 221/48 |
| 2006/0273100 A1 * | 12/2006 | Cittadino | A47K 10/426 221/33 |
| 2007/0284387 A1 | 12/2007 | Ellswood et al. | |
| 2007/0290094 A1 * | 12/2007 | Anderson | A47K 10/3836 242/594 |
| 2008/0061073 A1 * | 3/2008 | Laroche | A47K 10/421 221/63 |
| 2008/0245812 A1 | 10/2008 | Rogow et al. | |
| 2009/0261001 A1 | 10/2009 | Yao et al. | |
| 2011/0192861 A1 | 8/2011 | Bates et al. | |
| 2012/0068027 A1 | 3/2012 | Tyner | |
| 2014/0217112 A1 * | 8/2014 | Young | A47K 10/422 221/45 |
| 2016/0023838 A1 | 1/2016 | Chu | |
| 2016/0152403 A1 | 6/2016 | Ray | |

FOREIGN PATENT DOCUMENTS

| | | | | |
|---|---|---|---|---|
| GB | 2528242 A | * | 1/2016 | A61B 42/40 |
| KR | 20160045545 A | * | 4/2016 | F25D 23/06 |
| WO | 2011017496 | | 2/2011 | |
| WO | WO-2011017496 A2 | * | 2/2011 | B65D 83/0817 |

\* cited by examiner

CONTAINER FOR HOLDING AND DISPENSING MEDICAL GLOVES OR OTHER CONSUMABLES

CROSS-REFERENCE TO RELATED APPLICATIONS

This application claims the benefit of U.S. Provisional Patent Application No. 62/923,339, filed on Oct. 18, 2019, which is incorporated by reference herein in its entirety.

FIELD OF THE INVENTION

The present invention relates generally to holders for boxes of medical gloves or other consumables, and more particularly, to a container for storing and dispensing medical gloves or other consumables while also protecting the medical gloves or consumables from contamination prior to use or while being dispensed from the container.

BACKGROUND OF THE INVENTION

It is important in most medical procedures to use and wear protective medical gloves to prevent the transmission of diseases between a patient and medical care personnel. The medical care personnel don the medical glove prior to having any contact with the patient. Once the medical procedure ends, the medical gloves are then discarded. These single-use medical gloves are consumed in dozens by each medical professional daily, and constitute a significant expense for medical organizations.

Medical gloves are typically provided in bulk and are supplied in glove boxes having a small dispensing opening to manually pull the gloves out of the boxes. It is often inconvenient and messy to have one or more glove boxes lying around a patient's room or other medical facility area. Additionally, when not actually being accessed, the gloves in the boxes are constantly exposed, through the small dispensing openings, to various contaminants such as, for example, dust, dirt and even biological contaminants present in the room. Once contaminated, the gloves are of no use and are thrown away. Waste of the surgical gloves due to contamination is costly.

Further, the medical gloves are packed fairly tightly within the glove boxes such that when drawing out one medical glove, several other medical gloves are often accidentally also pulled out at the same time. If the medical personal are not careful, the accidentally pulled out, excess gloves may fall on non-sterile surfaces such as, for example, unclean tables or floors, and thus be contaminated requiring disposal as well. As those skilled in the art are aware, accidental dropping or falling of single-use medical gloves is so frequent that it can add up to hundreds of accidentally-dropped, single-use medical gloves having to be disposed on a weekly basis in any fairly-sized given medical facility and causing a significant money loss.

Accordingly, there remains a need for a solution to at least one of the aforementioned problems. For example, there is an established need for a sanitary and safe medical glove box container and dispenser that can protect the medical gloves container therein from contamination prior to being dispensed from the glove boxes. In another example, there is an established need for a medical glove box container and dispenser that can reduce or eliminate the risk of medical gloves having to be disposed due to accidental falling of the medical gloves from the container.

SUMMARY OF THE INVENTION

The present invention is directed to a convenient, protective container for receipt of one or more boxes of medical gloves or other consumables. The container is configured to allow the dispensing therefrom of the medical gloves or consumables contained in the box or boxes, and to catch any medical gloves or consumables dispensed from the boxes, and accidentally dropped, before they land on the ground and are contaminated. The container includes a box holder having a dispensing opening in a front panel of the box holder and a movable cover or tray which can be moved from a first or undeployed condition to a second or deployed condition extending outwardly from a front side of the box holder and substantially perpendicular to a vertical plane. The movable tray may be pivotally attached to the box holder or may be slidable mounted within the box holder. When pivotally mounted to the box holder, the movable tray covers the dispensing opening and protects the medical gloves or other consumables from dust and other contaminants when the movable tray is in the first condition.

In a first implementation of the invention, a container for retaining one or more boxes and dispensing medical gloves or other consumables contained in the one or more boxes comprises a hollow box holder and a movable panel. The hollow box holder comprises an interior cavity for receipt of one or more boxes of consumables. One or more dispensing openings are formed in a front side of the box holder and are arranged in spatial communication with the interior cavity. The movable panel is connected to the box holder and is movable relative to the box holder between a undeployed condition to a deployed condition. In the deployed condition, the movable panel is arranged extending outward of the glove box holder, with a surface of the movable panel facing upward and providing an area configured to capture one or more consumables fallen out of the interior cavity through the one or more dispensing openings of the box holder.

In a second aspect, the box holder may include a front panel, a rear panel, a first side panel, a second side panel and a bottom panel. The front, rear, first side, second side and bottom panels may define the interior cavity of the box holder. The one or more dispensing openings may be comprised in the front panel.

In another aspect, a rear side of the box holder may be configured for attachment to a wall.

In another aspect, a top side of the glove box may be open and configured to allow the insertion therethrough of the one or more boxes into the interior cavity of the glove box.

In another aspect, the movable panel in the deployed condition may be arranged forming 90 degrees with a vertical plane.

In yet another aspect, the movable panel in the deployed condition may form less than 90 degrees with a vertical plane.

In another aspect, the movable panel may be pivotably attached to the box holder and may be pivotable between the undeployed condition and the deployed condition. The movable panel in the undeployed condition may be arranged over the one or more dispensing openings of the box holder and encloses the interior cavity of the box holder. The movable panel in the deployed condition may be pivoted outward and downward relative to the undeployed condition and may be located below the one or more dispensing openings of the box holder.

In another aspect, the movable panel may be pivotable relative to the box holder about a rotation axis located at a bottom end of the box holder.

In another aspect, a bottom end of the movable panel may abut against a bottom of the box holder when the movable panel is in the deployed condition, preventing a further downward rotation of the movable panel.

In yet another aspect, the movable panel may be pivotably attached to the box holder by a pair of pivot pins.

In another aspect, the movable panel may be secured to the hollow box holder in the undeployed position by at least one disconnectable fastener.

In another aspect, the movable panel may include first and second side edges at opposite sides of the surface of the movable panel, the first and second side edges forming a respective angle with the surface such that the first and second side edges retain one or more consumables within the surface of the movable panel when the movable panel is in the deployed configuration.

In another aspect, the first and second side edges may be perpendicular to the surface of the movable panel.

In yet another aspect, the box holder may include one or more elastically flexible flaps extending into the interior cavity of the box holder and configured to adjustably position the one or more boxes of consumables against the front side of the box holder.

In another aspect, the one or more elastically flexible flaps may include a plurality of flaps arranged in one or more columns.

In another aspect, the one or more elastically flexible flaps may extend from respective one or more slots formed in the glove box.

In another aspect, the one or more slots may be formed in a rear side of the glove box.

In yet another aspect, each dispensing opening of the one or more dispensing openings may face and extend along a respective column of the one or more columns.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a safe and convenient container for holding and dispensing medical gloves or other consumables. The container is capable of holding multiple boxes of medical or surgical gloves or other consumables, hereinafter referred to generically as gloves, in a manner that protects the gloves from airborne contamination and prevents gloves removed in excess or accidentally removed from one of the boxes from falling on the ground.

Figure 1:
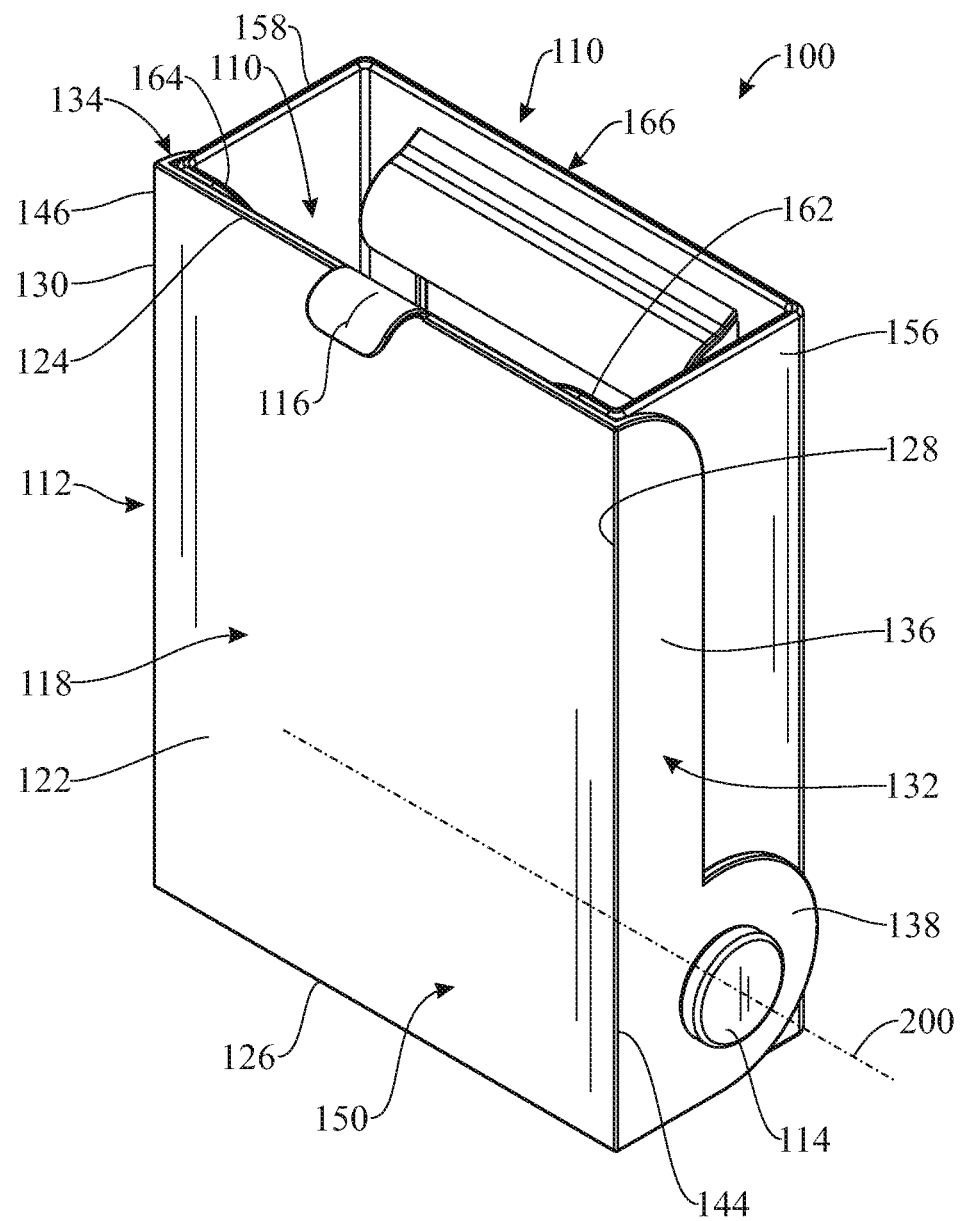
FIG. 1 presents a top, front isometric view of a container for storing and dispensing medical gloves or other consumables, in accordance with a first illustrative embodiment of the present invention, with a movable cover of the container shown in a closed position relative to a box holder of the container.
Figure 2:
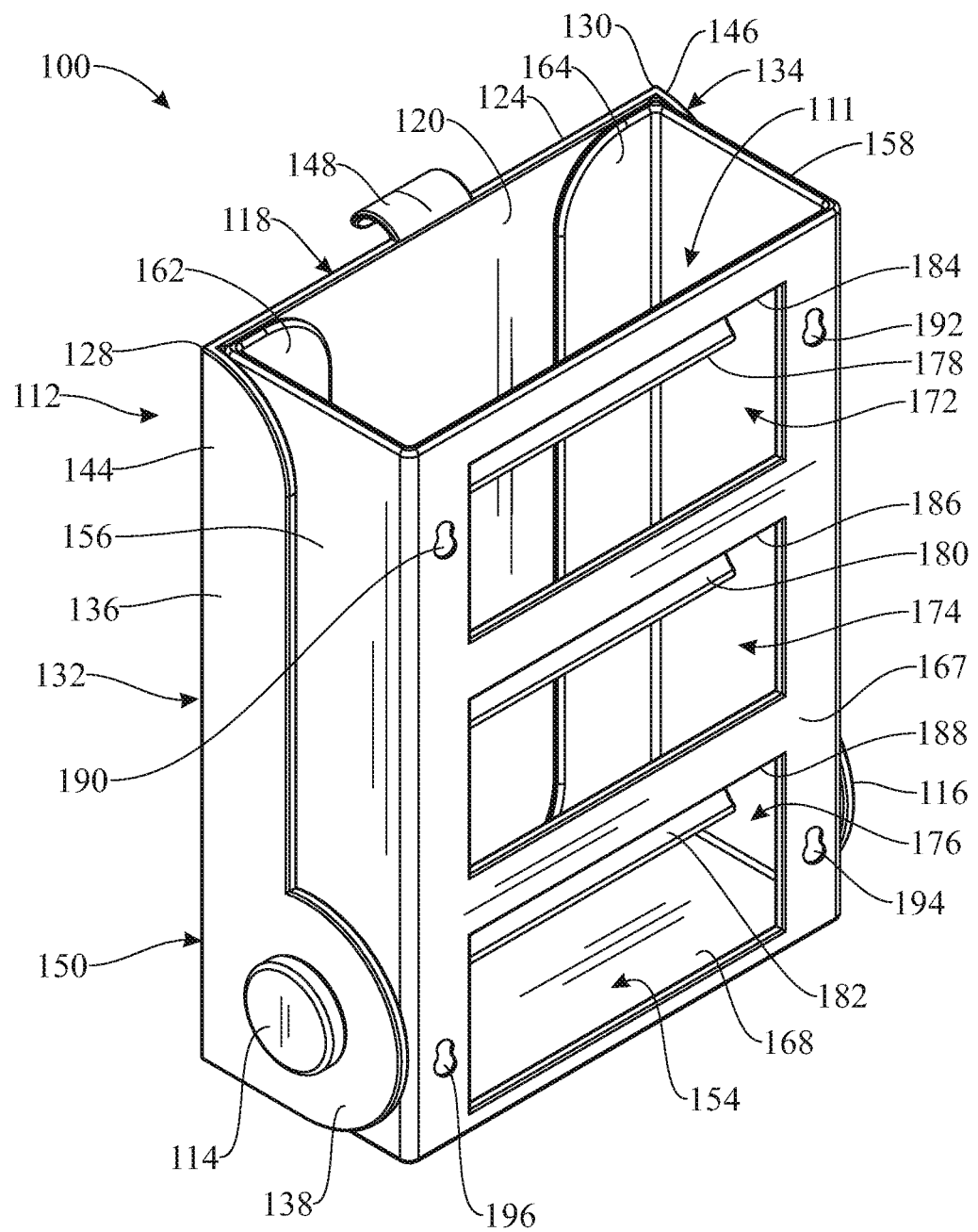
FIG. 2 presents a top, rear isometric view of the container of FIG. 1, with the movable cover also shown in the closed position.
Figure 3:
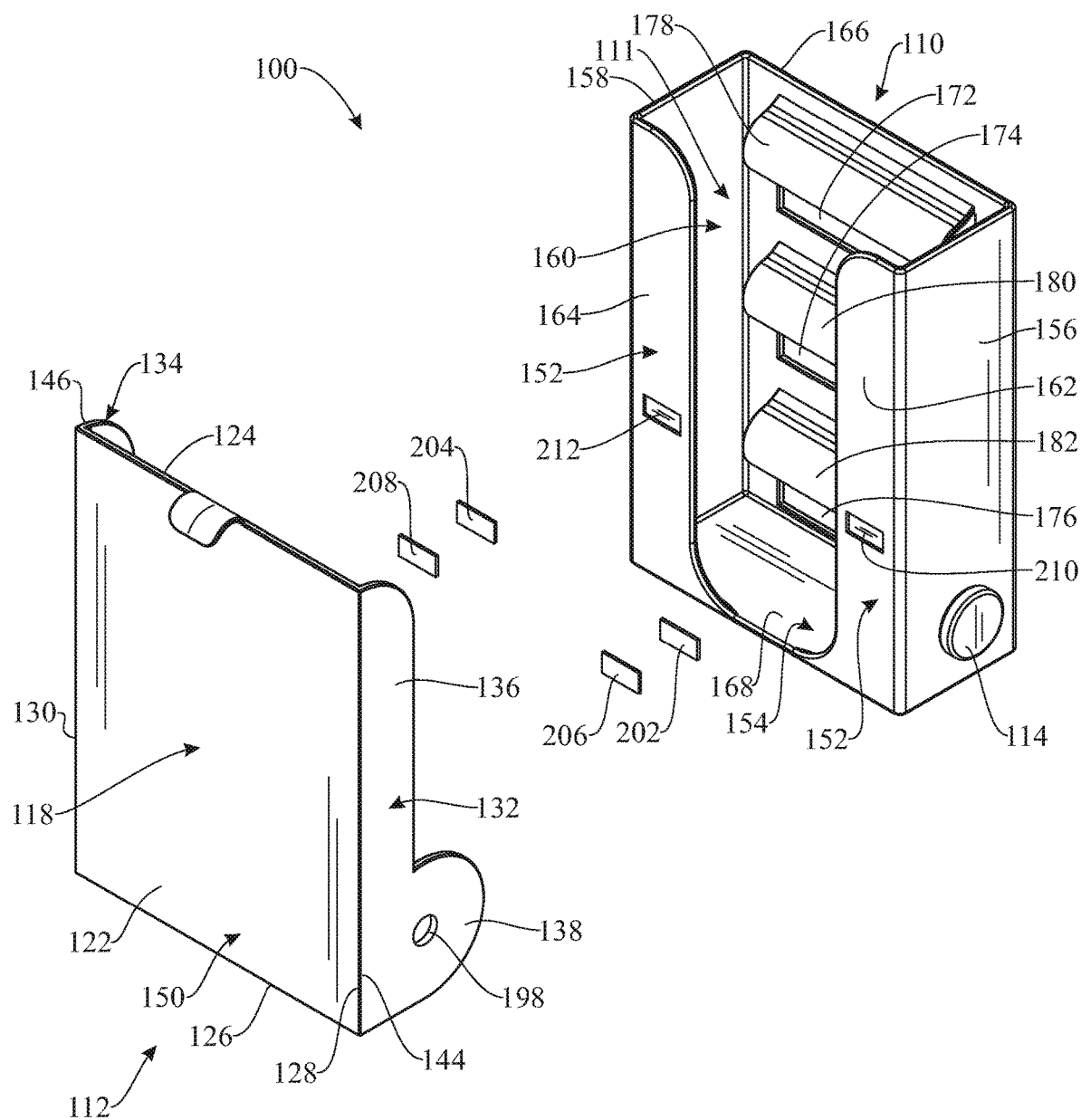
FIG. 3 presents an exploded top front isometric view of the container of FIG. 1, showing details of the box holder, movable cover and further revealing a set of retention strips.

Referring to FIGS. 1-7, and initially to FIGS. 1-3, a container 100 for storing and dispensing medical gloves or other consumables (hereinafter referred to generically as medical gloves) is illustrated in accordance with a first embodiment of the present invention. The container in accordance with the present invention is more specifically configured to house one or more boxes, each of which contains a plurality of medical gloves. Furthermore, the container 100 of the present embodiment is configured as a manually-operable and covered container for storing several boxes. As shown, the container 100 generally includes a hollow body or box holder 110 defining an interior cavity 111 for retaining a plurality of boxes, and a movable cover 112 pivotally mounted on the box holder 110 for protecting gloves in the boxes and catching any gloves that may fall out of the boxes as described in more detail hereinbelow. The movable cover 112 is pivotally attached to the box holder 110 by an articulated or hinged connection; for instance and without limitation, the articulated or hinged connection between the movable cover 112 and the box holder 110 can be provided by a pair of threaded knobs or pins 114 and 116. The container 100 may be formed of various plastics or polymers, metallic materials or any combination thereof preferably, the container is formed from an easily sterilizable material such as, for example, stainless steel.

As will be described in greater detail hereinafter, the movable cover 112 is provided to protect and catch gloves dispensed from boxes retained in the box holder 110. The movable cover 112 generally includes a front plate or panel 118 having and inner or tray surface 120 (FIG. 2) and an outer surface 122 (FIG. 1). The movable cover 112 catches and/or prevents wayward gloves from falling on the ground, and becoming contaminated and therefore unusable, when the movable cover 112 is pivoted to an open condition as described hereinbelow.

Figure 4:
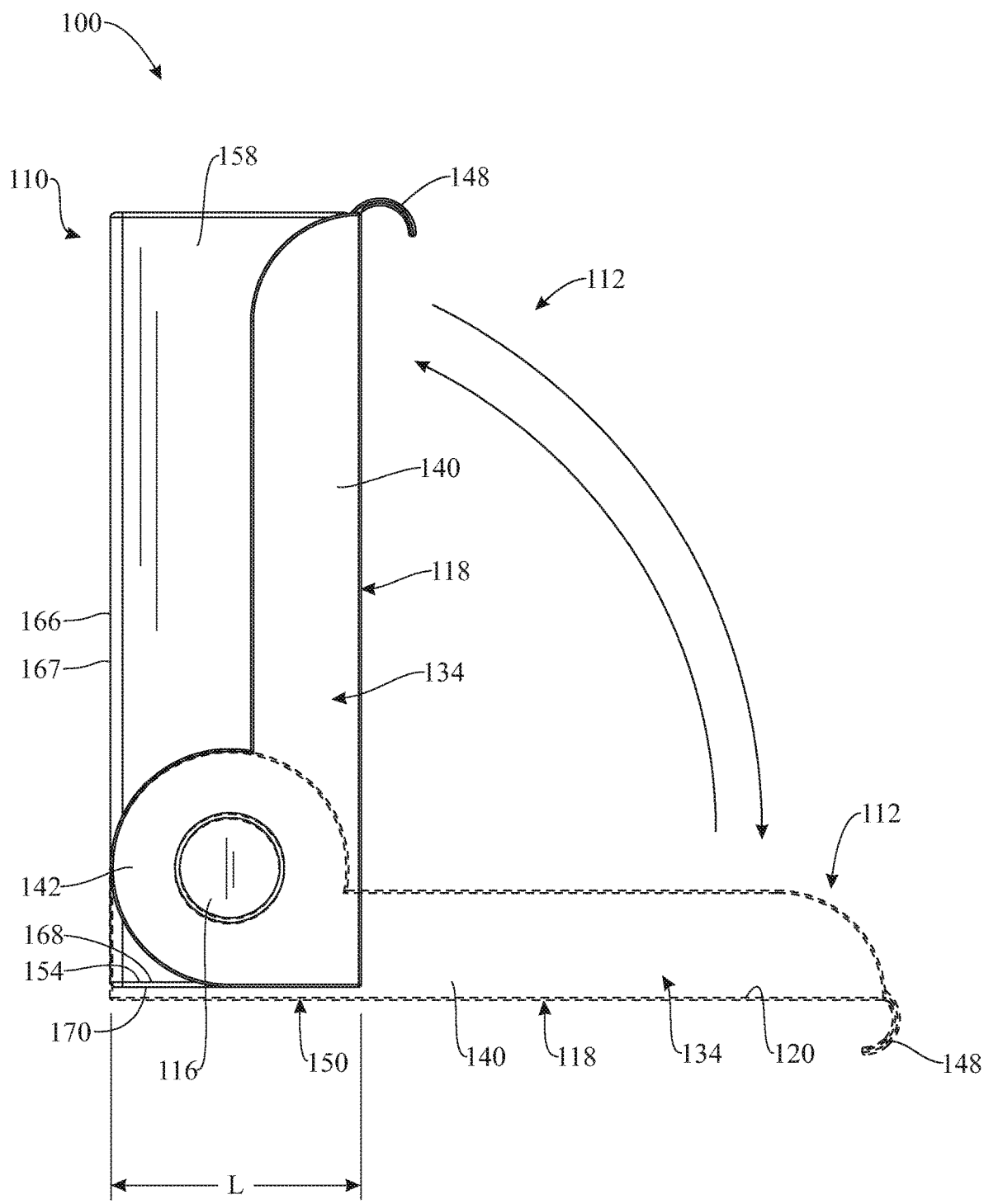
FIG. 4 presents a side elevation view of the container of FIG. 1, with the movable cover shown in the closed position (solid lines), and further shown in an open position (phantom lines) pivoted away from the box holder to provide a glove-catching surface or tray.

With continued reference to FIG. 1, the front panel 118 of the present embodiment is rectangular and has a top edge 124, a bottom edge 126 and first and second side edges 128 and 130. The movable cover 112 additionally includes a first side plate or panel 132 and a second side plate or panel 134. The first and second side panels 132 and 134, respectively, surround or embrace the box bolder 110 on the sides thereof and help secure the front cover 112 to the box holder 110 in friction fit fashion. The first side panel 132 includes a first longitudinal portion 136 and a first projection portion 138 extending rearwardly from the first longitudinal portion 136. Likewise, as best shown in FIG. 4, the second side panel 134 includes a second longitudinal portion 140 and a second projection portion 142 extending rearwardly from the second longitudinal portion 140.

The first and second side panels 132 and 134 may extend from the front panel 118 at an angle with the front panel 118. For example, the first side panel 132 of the present embodiment extends perpendicularly and rearwardly from the first side edge 128 of the front panel 118 and is secured thereto or integrally formed therewith along a first leading edge 144 of the first side panel 132. Similarly, the second side panel 134 extends perpendicularly and rearwardly from the second side edge 130 of the front panel 118 and is also secured thereto or integrally formed therewith along a second leading edge 146 of the second side panel 134 (FIG. 4). The pivot pins 114 and 116 extend through the first and second projection portions 138 and 142 of the first and second side panels 132 and 134, respectively. A pull tab 148 is provided at the top edge 124 of the front panel 118 to facilitate pulling and pivoting the front cover 112 with respect to the box holder 110. The pull tab 148 can extend frontward of the front panel 118, as shown.

As further shown in FIG. 1, the front panel 118 of the movable cover 112 additionally includes a lower or stop portion 150. As best shown in FIG. 4, the lower or stop portion 150 of the front panel 118 engages the box holder 110 when the movable cover 112 is moved to the open condition to prevent the movable cover 112 from pivoting beyond the open condition (e.g., with the front panel 118 pivoted 90° frontward and downward from the closed condition, also shown in FIG. 4). In the open condition of the movable cover 112, the inner or tray surface 120 of the front panel 118 forms a catch surface to catch loose gloves and prevent them from falling to the ground as described in more detail hereinbelow.

With continued reference to FIGS. 1-3, and in particular to FIGS. 2 and 3, the box holder 110 of the present embodiment is generally rectangular and box-shaped and includes a front panel 152, a bottom panel 154 and first and second side panels 156 and 158. The front panel 152 defines a dispensing opening or slot 160, which is in spatial communication with the interior cavity 111 of the box holder 110, and through which gloves contained within boxes in the container 100 may be withdrawn. Specifically, the front panel 152 includes first and second inwardly directed front panel portions 162 and 164 which define the slot 160 therebetween. The first and second inwardly directed front panel portions 162 and 164 and slot 160 can be elongately formed in a vertical direction, as shown. The box holder 110 additionally includes a rear panel 166 arranged in a spaced-apart relationship with the front panel 152, with the bottom panel 154 and first and second side panels 156 and 158 extending between the front panel 152 and the rear panel 166. The bottom panel 154 includes a top or inner surface 168 which may be configured to support or hold one or more boxes, and an opposite, bottom or outer surface 170 (FIG. 4) which engages the stop portion 150 of the front panel 118 of the movable cover 112 to prevent the movable cover 112 from pivoting beyond a maximum extended, tray-like position when the movable cover 112 is moved to an open condition relative to the box holder 110. In the extended, tray-like position, the movable cover 112 may form 90° with a vertical plane (e.g., a plane parallel to the rear panel 166, and more specifically, to a flat rear surface 167 of the rear panel 166 that may be configured to rest against a wall or other vertical surface).

With continued reference to FIGS. 2 and 3, the rear panel 166 can include one or more slots and associated inwardly-directed members or flaps configured to retain one or more corresponding boxes in place within the box holder 110. For example, the rear panel 166 of the present embodiment defines a first slot 172, a second slot 174 and a third slot 176 arranged in vertical alignment, one on top of the other, and a respective first flap 178, second flap 180 and third flap 182, also in vertical alignment with each other. The first, second and third flaps 178, 180 and 182, respectively, extend inwardly from respective top edges 184, 186 and 188 of the first, second and third rear slots 172, 174 and 176. The inwardly-directed flaps 178, 180 and 182 are provided to hold three boxes in place within the box holder 110, one on top of the other. To provide a secure grip of the glove boxes 300, the inwardly directed flaps 178, 180 and 182 are preferably elastically flexible, such that they tend to flex inward and towards the movable cover 112. The inwardly directed flaps 178, 180 and 182 of the present embodiment are integral with the rear panel 166 and are formed by stamping out the rear panel 166 to form the first, second and third slots 172, 174 and 176, respectively. Alternative embodiments are contemplated, however, in which the inwardly directed flaps 178, 180 and 182 are affixed or attached to the top edges 184, 186 and 188 of the first, second and third slots 172, 174 and 176 such as by gluing, welding, mechanical fasteners, magnetic fasteners, or combinations thereof, for instance and without limitation.

With specific reference to FIG. 2, the rear panel 166 of the box holder 110 may be provided with mounting holes 190, 192, 194 and 196 to allow the container 100 to be mounted to a wall. The mounting holes 190, 192, 194 and 196 may be used to receive screws, bolts, etc. therethrough or may be used to mount the container 100 on mounting studs affixed to a wall or other mounting surface, such as, but not limited to, medical carts, doors, cabinets, etc. The disconnectable wall or surface attachment enabled by the mounting holes 190, 192, 194 and 196 renders the container portable and capable of being relocated from room to room or about a room for the convenience of the user(s). In some embodiments, the rear surface 167 of the rear panel 166 may be flat, as shown, and configured to substantially rest on a wall, to further stabilize the container 100.

Referring again to FIG. 3, the movable cover 110 includes a pair of pivot holes 198 formed through the respective first and second projection portions 138 and 142 of the first and second side panels 132 and 134. The pivot holes 198 are provided to receive the pivot pins 114 and 116 and pivotally secure the movable cover 112 to the box holder 110 about a transverse rotation axis 200, i.e. a rotation axis arranged in a left-to-right direction as shown in FIG. 1. Additionally, as further shown in FIG. 3, releasable fasteners 202, 204, 206 and 208 may be provided on the box holder 110 and the movable cover 112 to hold the movable cover 112 against the box holder 110 when the movable cover 112 is in the up or closed condition. The releasable fasteners 202 and 204 may be attached directly to the front panel 152, such as affixed within recesses 210 and 212 formed in the first and second front panel portions 162 and 164 of the front panel 152. The releasable fasteners 202, 204, 206 and 208 may be in the form of magnets, hook-and-loop fasteners, etc.

As best shown in FIG. 4, in operation, the movable cover 112 is movable between a first or closed condition covering the front panel 152 and dispensing slot 160 of the box holder 110 and a second or open condition exposing the one or more boxes housed inside the box holder 110, and thereby exposing the gloves contained within the one or more boxes, through the dispensing slot 160. Opening of the movable cover 112 can be accomplished by pulling on the pull tab 148 to pivot the movable cover 112 away from the box holder 110. As the movable cover 112 is pivoted away from the box holder 110 and about the transverse rotation axis 200, the lower or stop portion 150 of the front panel 118 eventually contacts or abuts against the outer surface 170 of the bottom panel 154 of the box holder 110 thereby preventing the movable cover 112 from pivoting downward any further; said contact or abutment may occur, for instance, with the movable cover 112 at a 90° angle relative to a vertical plane, as shown, said contact or abutment thus holding the movable cover 112 at said 90° angle. In this open position, the front panel 118 is arranged extending outward and forms a "tray" to catch any gloves that may inadvertently be pulled out of boxes and prevent them from landing on the ground by having them instead fall on the inner surface 120 of the front panel 118. Thus, the movable cover 112 saves falling gloves from contamination on the ground, decreasing waste and saving money otherwise lost on contaminated and therefore unusable gloves. It should be noted that, in the present embodiment, the length "L" of the stop portion 150 of the front panel 118 is shown to be substantially equal to the length "L" of the bottom panel 154, such that the stop portion 150 extends over and abuts against the full length of the bottom panel 154, as shown in FIG. 4. While a shorter stop portion 150 may suffice to hold the movable cover 112 perpendicular to the box holder 110, by making them equal lengths maximum support is provided to the movable cover 112 to support the weight of fallen gloves or any other material that may inadvertently or purposefully be deposited on the inner or tray surface 120 of the front panel 118. It must be noted that alternative embodiments are contemplated in which the movable cover 112, when adopting the "tray" position (i.e. when opened and held in place by the stop portion 150), may be arranged in a slightly tilted position, i.e. forming an angle slightly less than 90° with a vertical plane (e.g., 80°), such as to prevent gloves caught by the tray from sliding frontward out of the tray (i.e. away from the rotation axis 200) while still providing a sufficiently large glove-catching surface area and not interfering with the dispensing of gloves through the dispensing slot 160.

Turning now to FIGS. 1 and 4-7, the use of the container 100 to retain one or more boxes 300 (FIGS. 5-7) of medical gloves 302 (FIG. 7), facilitate dispensing of the gloves 302, and prevent contamination or waste of the gloves 302 contained within the boxes 300, will now be described. Initially, with regard to FIG. 1, the container 100 is installed in place (e.g., on a cabinet or wall), and the movable cover 112 of the container 100 is in a closed of first condition flush against the box holder 110.

Figure 5:
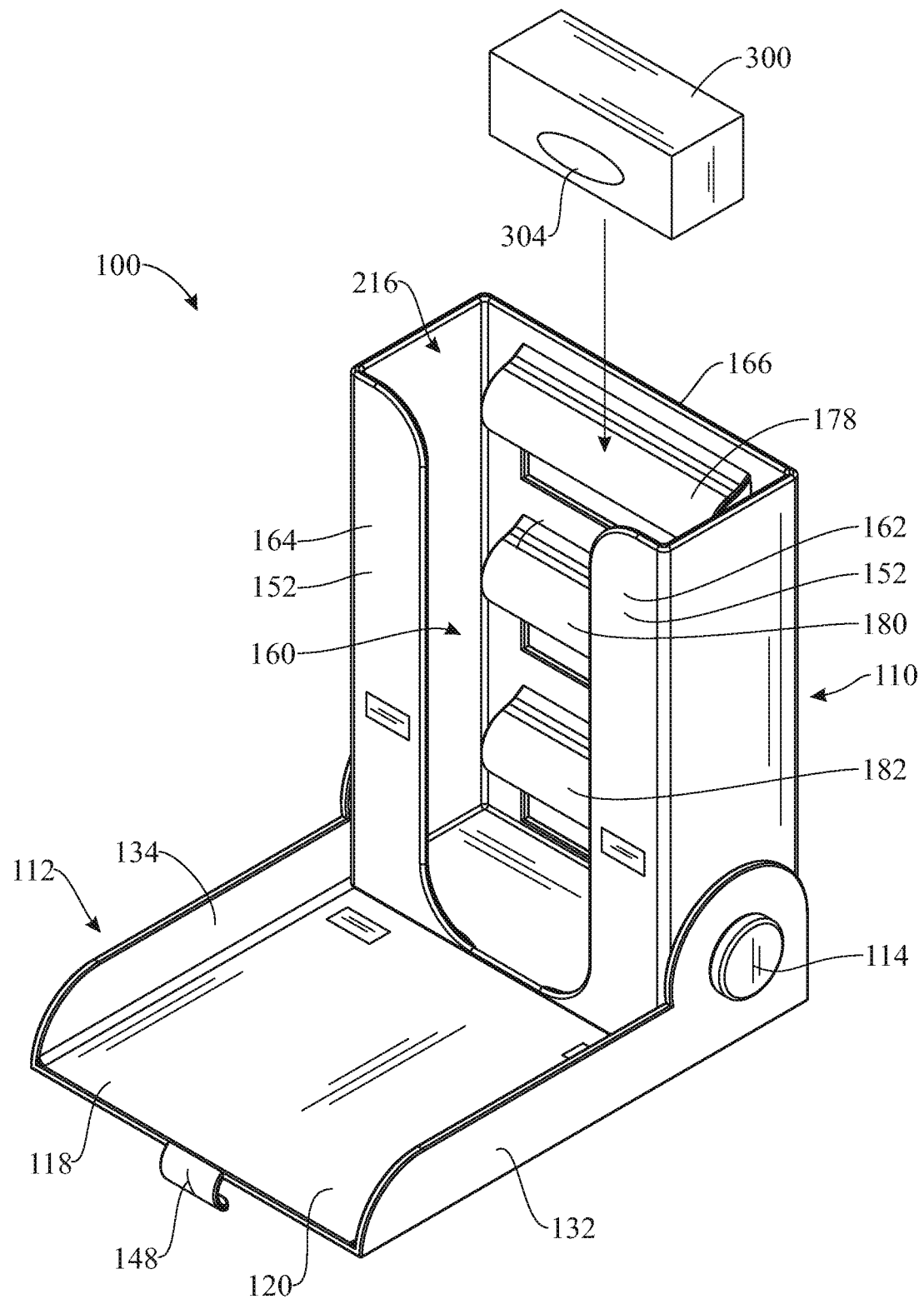
FIG. 5 presents a top, front isometric view of the container of FIG. 1, with the movable cover pivoted to an open or down condition and a box of medical gloves being inserted into the box holder.
Figure 6:
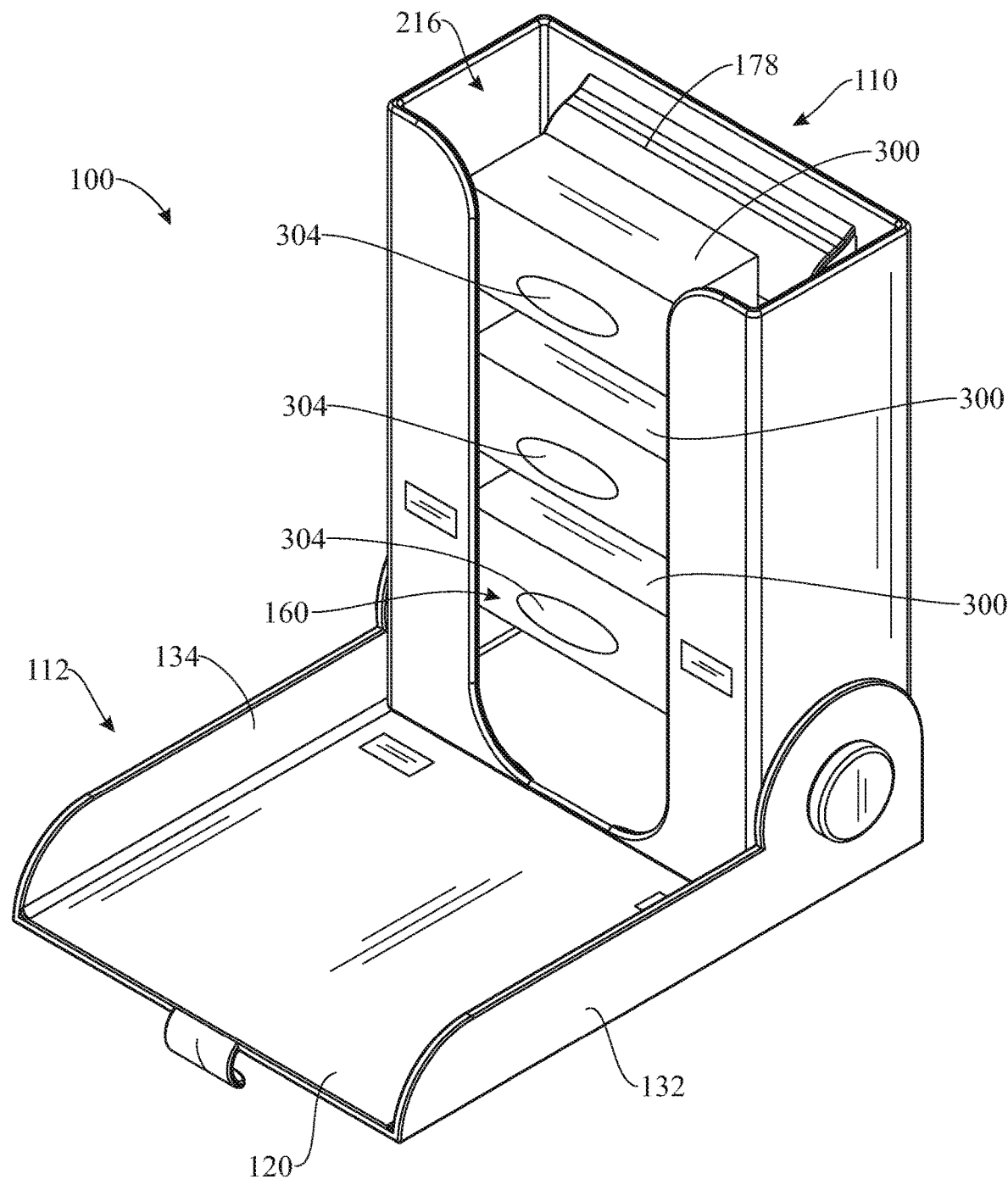
FIG. 6. presents a top, front isometric view of the container, similar to FIG. 5, with multiple boxes of medical gloves inserted into the box holder in a vertically-aligned relationship with one another.

As shown in FIG. 5, a glove box 300 is inserted into the interior cavity 111 of the box holder 110 through an open top area 216 of the box holder 110 and moved down in the box holder 110 to position a dispensing opening 304 of the glove box 300 in line with the dispensing slot 160 of the box holder 110 (FIG. 6). In some cases, the glove box 300 may be inserted through the open top area 216 with the movable cover 112 in the closed or first condition. In other cases, the user may choose to open the movable cover 112 prior to inserting the glove box 300, in which case, as best shown in FIG. 4, the pull tab 148 is manipulated to pivot the movable cover 112 frontward and outward about the rotation axis 200, from the closed or first condition to an open or second condition exposing the front panel 152 of the box holder 110.

Figure 7:
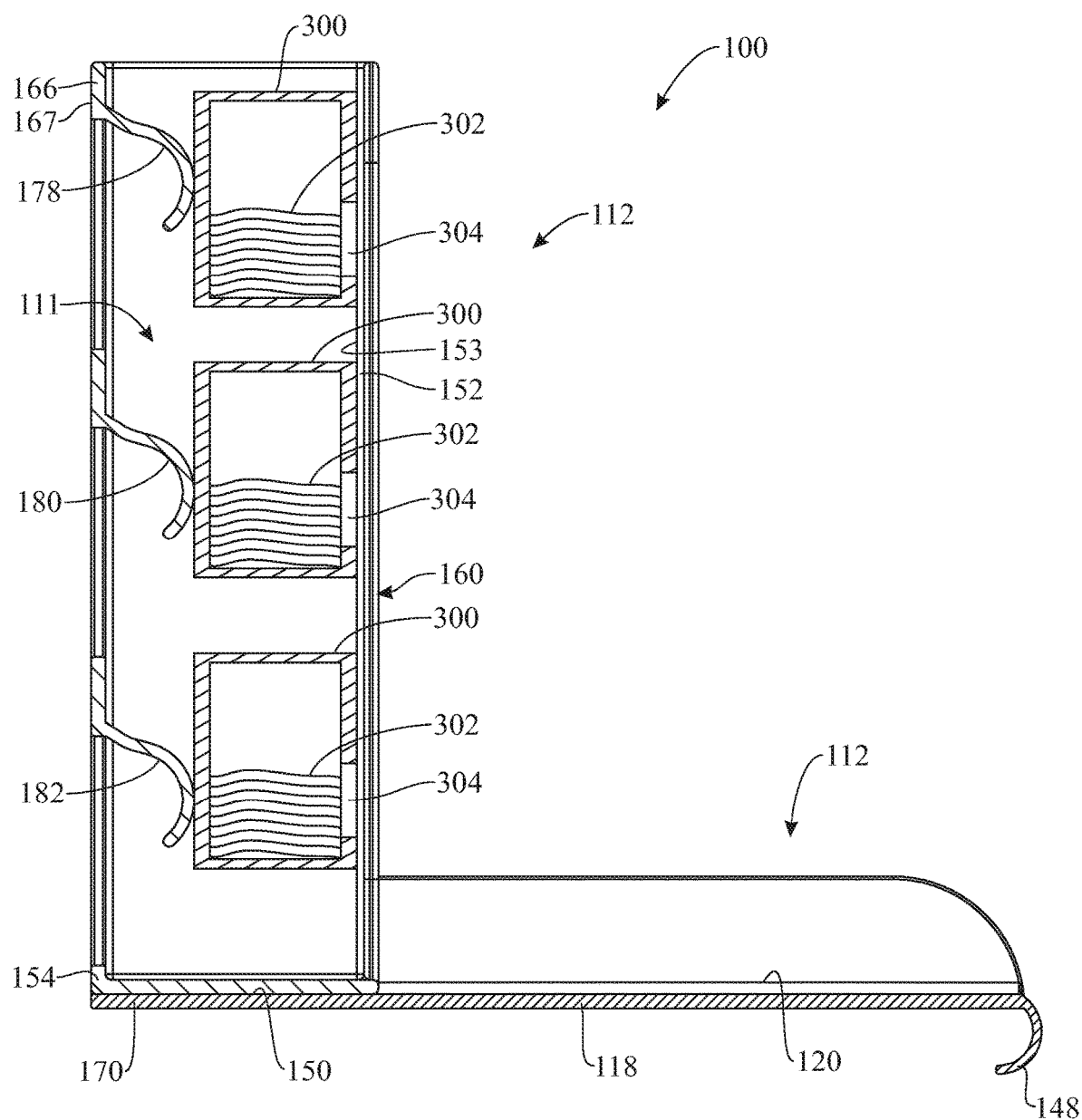
FIG. 7 presents a cross-sectional side elevation view of the container of FIG. 1 with the movable cover in the open condition and the multiple boxes of medical gloves inserted into the box holder.

As depicted in FIGS. 5 and 7, the glove box 300 is held in place by one of the first, second and third flaps 178, 180, 182. For example, as shown, the glove box 300 may be retained between said one of the first, second and third flaps 178, 180, 182 and an inner side or surface 153 of the front panel 152 of the box holder 110. Preferably, the flaps are elastically deformable such that they provide a forward pushing force on the glove box 300 to increase friction between the glove box 300 and the inner surface 153, and between the glove box 300 and the flap. In this embodiment, the container 100 is configured to retain three glove boxes 300, wherein each glove box 300 is secured in place by a respective one of the first, second and third flaps 178, 180, 182. Alternatively, the container 100 may be configured to retain more or fewer than three glove boxes 300. It must be noted that the glove boxes 300 may vary in shape and/or size, and that the elastically flexible nature of the first, second and third flaps 178, 180 and 182 allows the first, second and third flaps 178, 180 and 182 to adjustably push the glove boxes 300 forward, onto the inner surface 153 of the front panel 152, and to thereby retain glove boxes 300 of varying sizes within the box holder 110. Once the box holder 110 has been loaded with one or more glove boxes 300, the movable cover 112 can then be pivoted back to the up or closed condition of FIGS. 1 and 2, flush against the first and second side panels 156 and 158 of the box holder 110 thereby covering the dispensing slot 160 and preventing dust or other contaminants from reaching the gloves 302 in the glove boxes 300.

When it is desired to access and pull out gloves 302 from a glove box 300, the movable cover 110 is pivoted to the open or second condition (FIGS. 5 and 6) as described hereinabove. The gloves 302 may then be pulled free of the glove boxes 300 through the dispensing openings 304 and the aligned, dispensing slot 160. The first and second front panel portions 162 and 164 of the front panel 152 retain the glove boxes 300 in place inside the box holder 110, thus facilitating frontward and outward pulling of the gloves 302 from the glove boxes 300. Due to the tightly packed nature of the gloves 302 in the glove boxes 300, on pulling out a single glove 302, other gloves 302 may inadvertently be pulled out of the glove box 300 together with the single glove 302. By limiting the opening of the movable cover 112 to 900 (or similar) relative to the box holder 110, the inner tray surface 120 of the front panel 118 is arranged in a position configured to catch any wayward gloves 302 before they fall to the ground. Additionally, the upward orientation of the first and second side panels 132 and 134 on either side of the front panel 118 when movable cover 112 is in the open condition allows the first and second side panels 132 and 134 to prevent any wayward gloves 302 from sliding off sideways off of the tray surface 120. In this manner, the container 100 serves a dual purpose: on one hand, when the movable cover 112 is closed, the container 100 protects gloves 302 from contamination prior to use; on the other, when the movable cover 112 is open and in the "tray" position, the container 100 facilitates dispensing of the gloves 302 by holding the glove boxes 300, and also catches any excess gloves 302 that may be pulled out of the glove boxes 300, which prevents the gloves 302 from being contaminated by contact with the floor, ground or other undesirable and non-sterile surface thereby decreasing waste and saving the user money.

Figure 8:
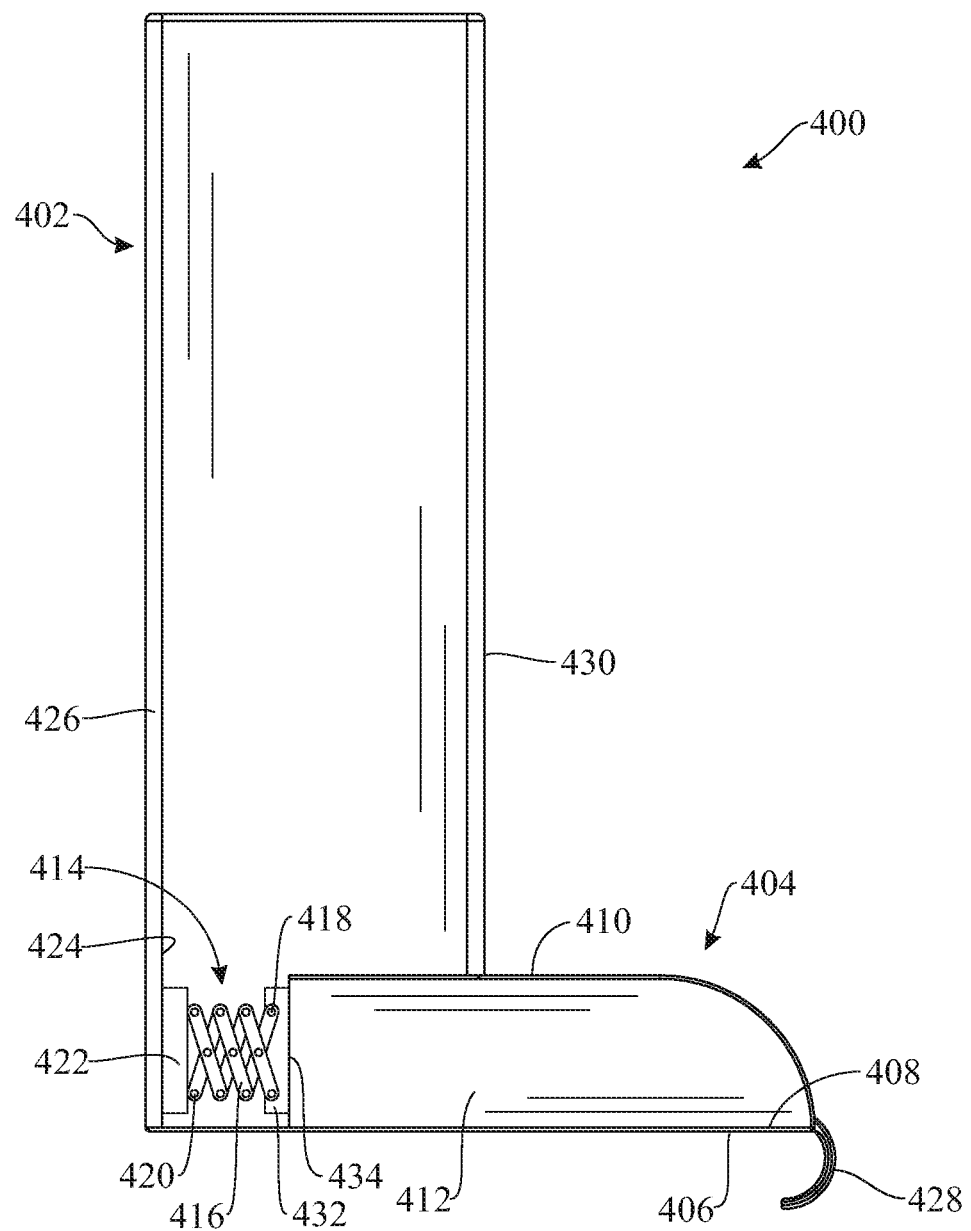
FIG. 8 presents a side elevation view of a container in accordance with a second illustrative embodiment of the present invention, the container including an extension mechanism enabling the pulling outward of the tray relative to the box holder.

Turning to FIG. 8, there is disclosed a container 400 for retention of the glove boxes 300 and protection of the gloves 302 contained therein, in accordance with a second illustrative embodiment of the present invention. The container 400 generally includes a box holder 402 for retention of glove boxes 300 and dispensing of gloves 302 and a movable tray 404 that extends substantially perpendicularly outward from the box holder 402 to catch any gloves 302 and prevent them from falling to the floor.

While not specifically shown, the box holder 402 is substantially similar to the box holder 110 described hereinabove and is configured to hold one or more glove boxes 300 for dispensing gloves 302 in similar manner. In this embodiment, the movable cover or tray 404 includes a horizontal tray plate 406 oriented perpendicular to the box holder 402 and having an upper tray surface 408 for catching any wayward gloves 302. The movable tray 404 additionally includes first and second side panels 410 and 412, respectively, extending upward from the tray plate 406 to prevent the gloves 302 from sliding off the tray plate 406.

The container 400 of the present embodiment includes an extension mechanism 414 for extending and retracting the movable tray 404 relative to the box holder 402. In this embodiment, the extension mechanism 414 consists of a scissor mechanism 416 having a first end 418 secured to the movable tray 404 and a second end 420 secured to a mounting plate 422 affixed to an inner surface 424 of a rear panel 426 of the box holder 402. A pull tab 428 is provided on the movable tray 404 to assist in extending and retracting the movable tray 404 relative to the box holder 402.

In use, the movable tray 404 is movable between a first condition retracted within or towards the box holder 402 and a second or extended condition wherein the movable tray 404 extends outwardly from and is substantially perpendicular, i.e. at approximately 90° relative, to a front panel 430 of the box holder 402 to catch any gloves 302 falling out of the glove boxes 300. Additionally, the extension mechanism 414 and specifically the first end 418 of the scissor mechanism 416 may be affixed to a second mounting plate 432 affixed to a rear plate 434 of the movable tray 404. It should be noted that, while the extension mechanism 414 is illustrated as the scissor mechanism 416, other extension mechanisms 414, such as, for example, spring mechanisms, magnetic mechanisms, electric, hydraulic and/or pneumatic mechanisms, etc. are also within the contemplated scope of the present invention. Furthermore, the extension mechanisms may be used in combination with an articulated coupling of the movable cover and the box holder; i.e., in some embodiments, the movable cover may be pivotably coupled to the box holder to pivotally adopt a closed position and an open, "tray" position (similarly to movable cover 112), and also configured to extend frontward and outward of the box holder when in the "tray" position, to increase the effective "tray" or glove-catching surface area of the movable cover (similarly to movable cover or tray 404).

Figure 9:
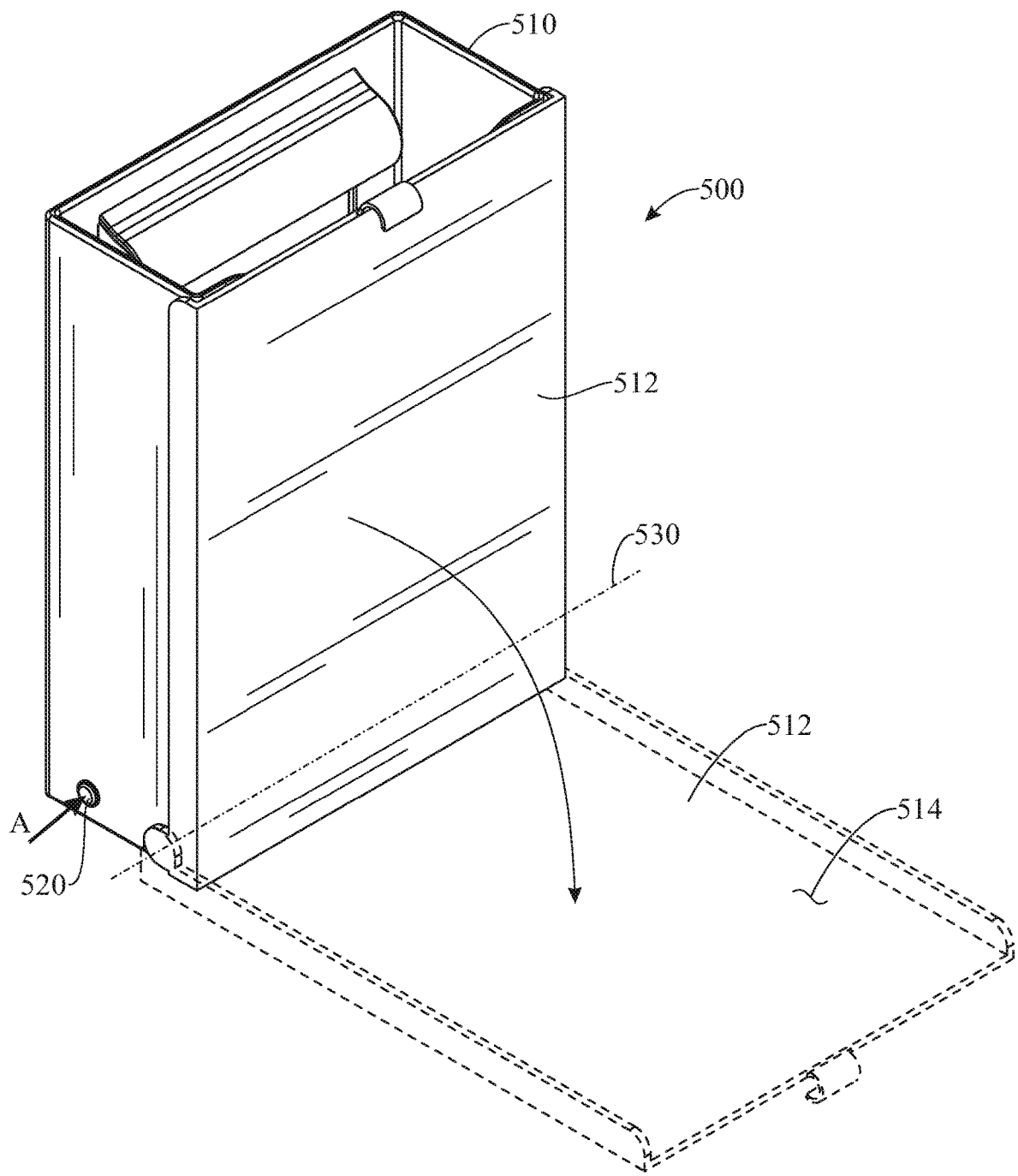
FIG. 9 presents a top, front isometric view of a container for storing and dispensing medical gloves or other consumables, in accordance with a third illustrative embodiment of the present invention, depicting movement of a hydraulically-actuated movable cover from a closed position towards an open position and/or from an open position towards a closed position.
Figure 10:
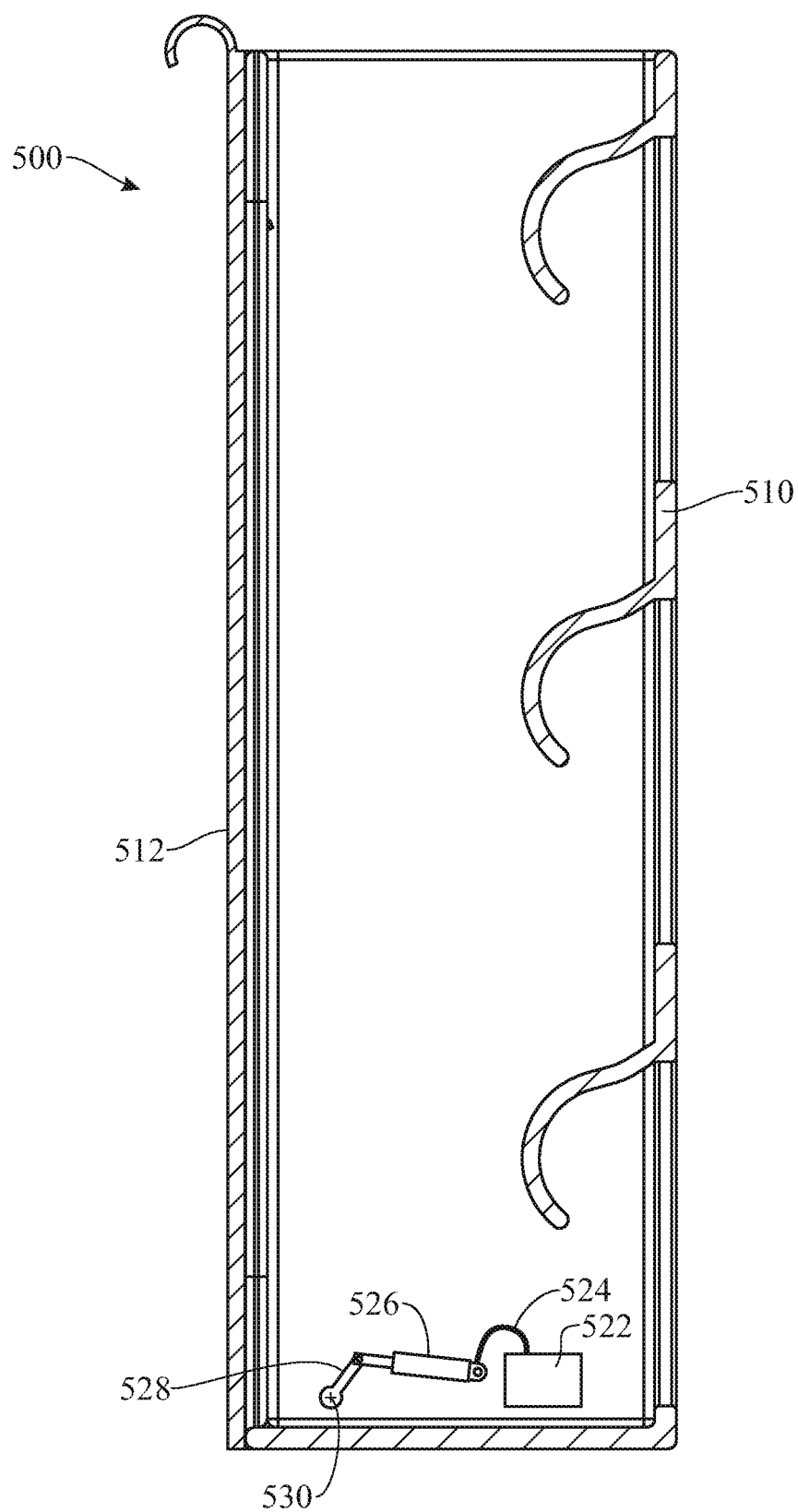
FIG. 10 presents a cross-sectional, side elevation view of the container of FIG. 9, with the movable cover in the closed position.
Figure 11:
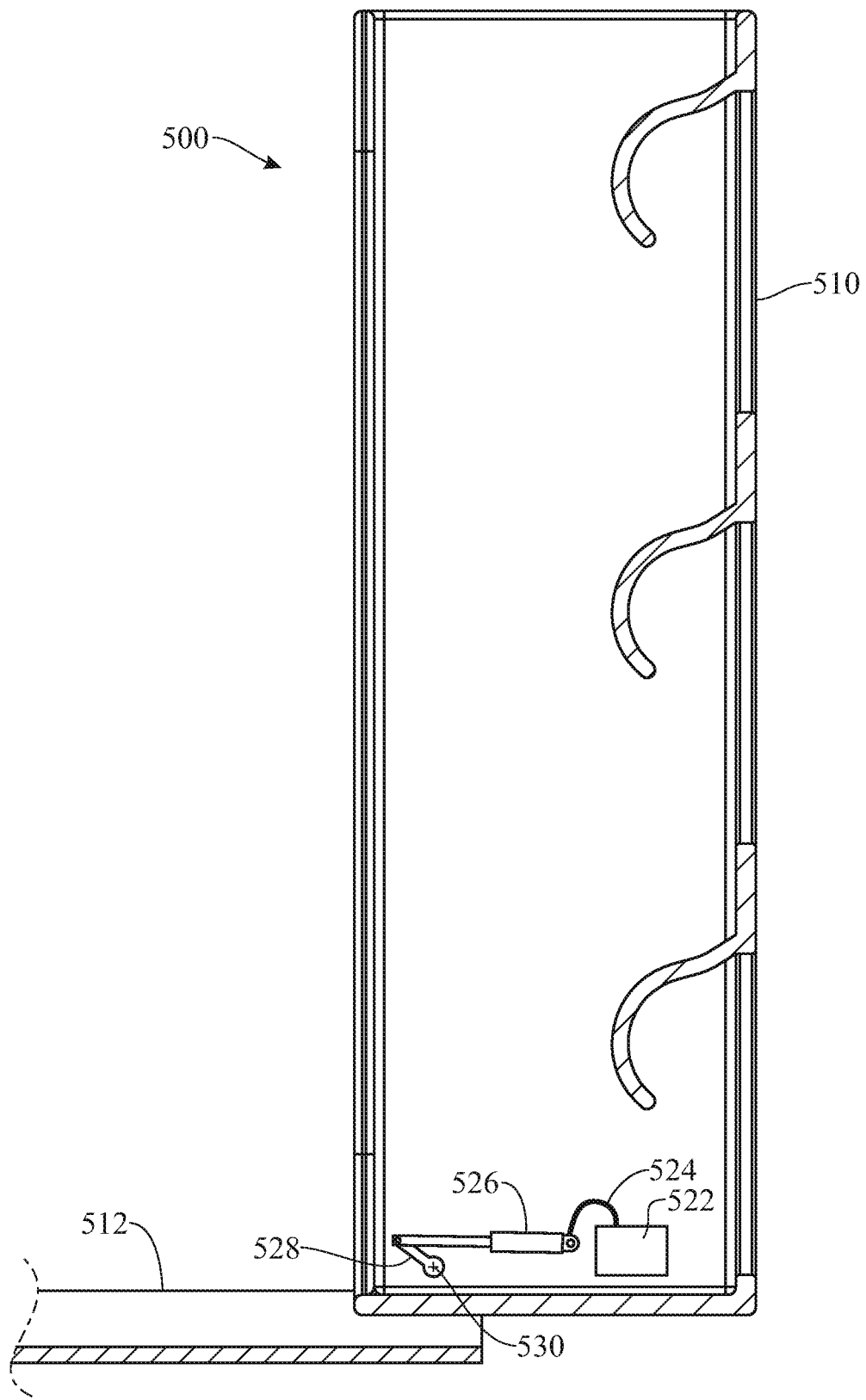
FIG. 11 presents a cross-sectional, side elevation view of the container of FIG. 9, with the movable cover in the open position.

The illustrations of FIGS. 9-11 show a container 500 for storing and dispensing medical gloves or other consumables, in accordance with yet another embodiment of the invention. With reference to FIG. 9, similarly to previous embodiments, the container 500 comprises a box holder 510 and a movable cover 512. The movable cover 512 is pivotably carried by the box holder 510 and is reversibly movable from a closed position to an open or tray position, shown in solid lines and in broken lines, respectively. In the open position, the movable cover 512 provides a tray-like structure having a clean, inner surface 514, such that gloves which may accidentally fall from the glove boxes can be retained on the inner surface 514, similarly to previous embodiments.

Unlike previous embodiments, however, movement of the movable cover 512 of the present embodiment is automated. More specifically, the container 500 is provided with a user-operable control 520 (e.g., a depressible button), a hydraulic fluid reservoir 522, a hydraulic fluid tubing 524 and a compressible and expandable hydraulic actuator 526. Fluid communication may be provided from the hydraulic fluid reservoir 522 and hydraulic cylinder or actuator 526, via the hydraulic fluid tubing 524, responsively to user operation of the user-operable control 520 (e.g., pressing the button as indicated by arrow A in FIG. 9). A distal end of the hydraulic actuator 526 may be pivotably connected to a link 528, in turn non-rotationally attached to the movable cover 512 such that the link 528 and movable cover 512 can rotate jointly about a rotation axis 530. When pressurized hydraulic fluid enters the hydraulic actuator 526 responsively to user operation of the user-operable control 520, the hydraulic actuator 526 expands, and the distal end of the hydraulic actuator 526 exerts a torque on the link 528 which causes the link 528 (and thus the movable cover 512) to rotate about the rotation axis 530 and thus the movable cover 512 to pivot from the closed position of FIG. 10 to the open position of FIG. 11. In some embodiments, once the user has retrieved one or more gloves from the box holder 512, the user may push the movable cover 512 upward towards the closed position, thereby exerting a torque on the movable cover 512, and said torque may rotate the link 528 back towards the hydraulic actuator 526, thereby compressing the hydraulic actuator 526 and feeding compressed hydraulic fluid back into the hydraulic fluid reservoir 522 through, for instance and without limitation, a one-way valve (not shown). In some embodiments, the movement of the movable cover 512 from the open position to the closed position may be hydraulically actuated instead. In other embodiments, both the movement of the movable cover 512 from the open position to the closed position, and the movement of the movable cover 512 from the closed position to the open position, may be hydraulically actuated. Further embodiments of the invention are contemplated in which the opening movement and/or the closing movement may be electrically- or pneumatically-actuated. In some embodiments, the user-operable control may be non-tactile (e.g., by a proximity sensor, or voice commands), to facilitate accessing the gloves housed within the device without touching or physically contacting the device.

As further shown in FIG. 9, the rotation axis 530 of the movable cover 512 is arranged at or near a front bottom edge of the box holder 510, which may contribute to maximize the surface area of the glove catching, inner surface 514. It must be noted that this and/or other features of the current embodiment may be applied to other embodiments described herein, as feature(s) of other embodiments may be applied to the present embodiment, without departing from the scope of the present disclosure.

Figure 12:
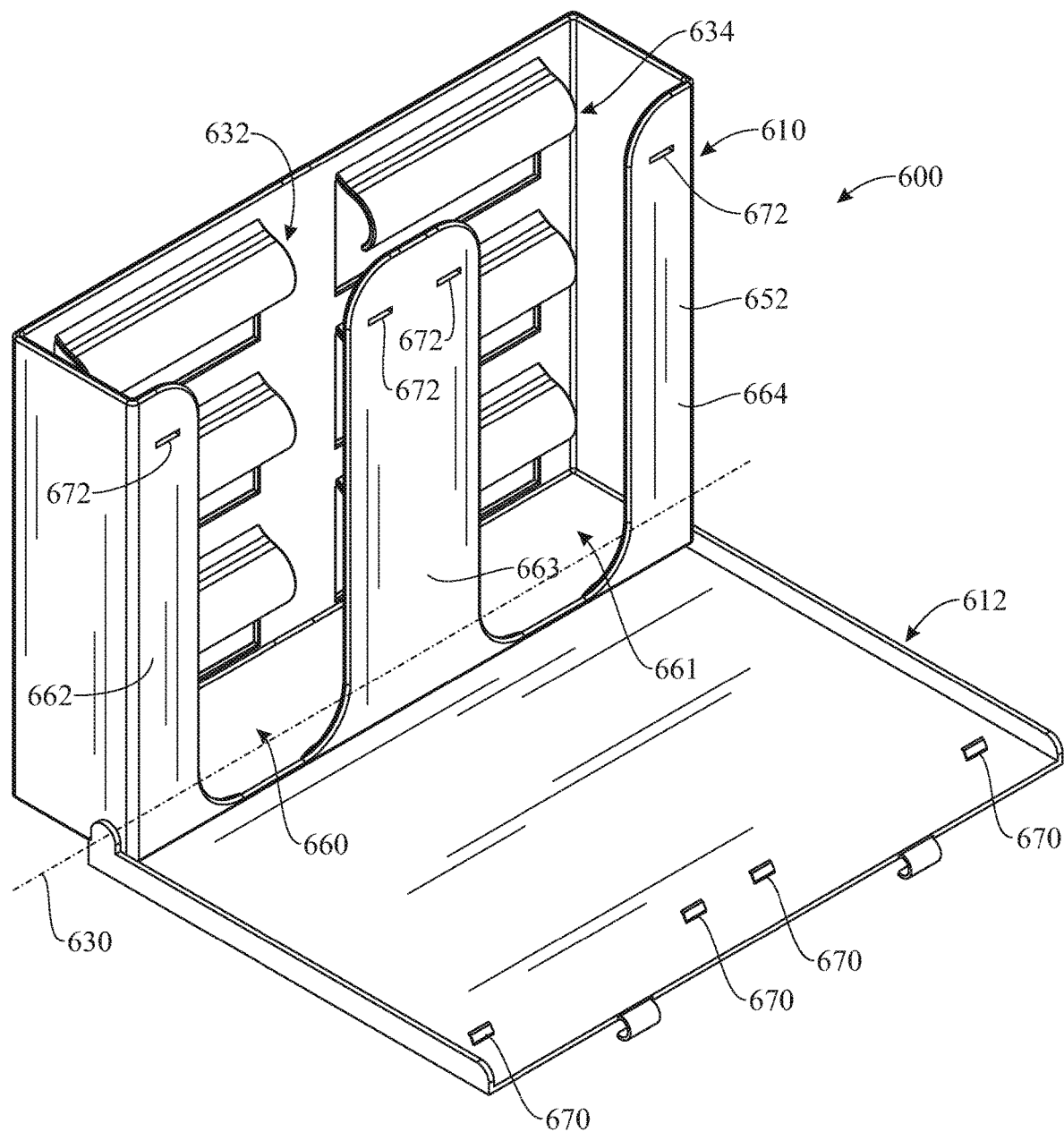
FIG. 12 presents a top, front isometric view of a container for storing and dispensing medical gloves or other consumables, in accordance with a fourth illustrative embodiment of the present invention, the container configured to house two columns of glove boxes and further comprising elastic tabs for securing the movable cover in the closed position.
Figure 13:
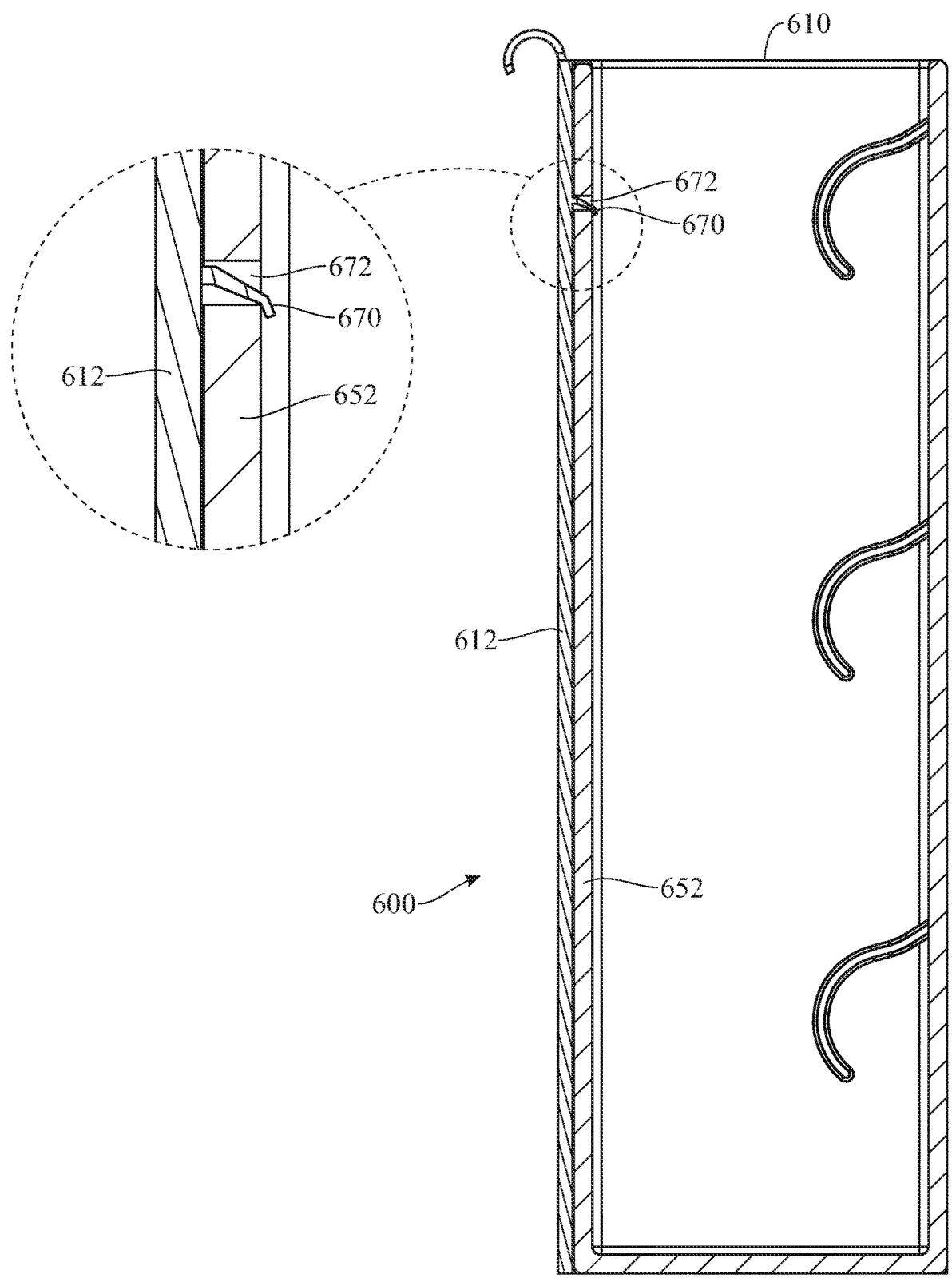
FIG. 13 presents a cross-sectional, side elevation view of the container of FIG. 12, together with an enlarged partial view of a top front area of the container, to further depict the elastic tabs.

The illustrations of FIGS. 12 and 13 show a container 600 in accordance with further embodiment of the invention, the container 600 including a box holder 610 and a movable cover 612 pivotably connected to the box holder 610 and movable between opened and closed positions, similarly to previous embodiments. As shown, the movable cover 612 is pivotable about a rotation axis 630 located at or near a bottom front edge of the box holder 610. The movable cover 612 is manually movable, i.e. configured to pivot upward and downward responsively to a torque exerted by a user's hand or hands on the movable cover 612. However, alternative embodiments are contemplated, such as having an electrically-, pneumatically- or hydraulically-operated movable cover.

As further shown, the container 600 of the present embodiment is relatively wider than those of previous embodiments and includes two sets of elastically flexible flaps 632 and 634 arranged in side-by-side relationship with one another. More specifically, a first set of flaps 632 includes a first series of three vertically aligned flaps configured to abut against three corresponding boxes (not shown), similarly to the embodiment of FIG. 1, and the second set of flaps 634 includes a second series of three vertically aligned flaps configured to abut against three additional boxes (not shown). I.e., the present embodiment includes six elastically flexible flaps arranged in a 3-row, 2-column configuration enabling six glove boxes to be secured in a corresponding 3×2 matrix configuration. Alternative embodiments are contemplated in which the container may include any number of elastically flexible flap rows and/or columns greater than or equal to one, to house and secure a corresponding number of glove boxes. As further shown, in embodiments where two or more columns are present, the front panel 652 of the box holder 610 may be divided into three or more front panel portions 662, 663 and 664 which are spaced-apart from one another such that a corresponding dispensing slot 660, 661 is defined between each pair of adjacent front panel portions. For example, first and second panel portions 662 and 663 may be arranged facing one another and spaced apart by a first dispensing slot 660, such that the first and second panel portions 662 and 663 retain a first column of boxes and the gloves contained therewithin may be retrieved through the first dispensing slot 660. Similarly, the second panel portion 663 and a third panel portion 664 may be arranged facing one another and spaced apart by a second dispensing slot 661, such that the second and third panel portions 663 and 664 retain a second column of boxes and the gloves contained therewithin may be retrieved through the second dispensing slot 661.

As further shown in FIGS. 12 and 13, the container 600 may further include one or more elastically flexible tabs 670 configured to disconnectably engage with corresponding tab-receiving spaces 672 to secure the movable cover 612 to the glove box 610 in the closed position. In some embodiments, such as the present embodiment, the one or more elastically flexible tabs 670 may be comprised in the movable cover 612, and the corresponding tab-receiving spaces 672 may be provided in the box holder 610. For example, the tabs 670 of the present embodiment are specifically provided at or near a distal end of the movable cover 612 opposite to the rotation axis 630, and the corresponding tab-receiving spaces 672 are formed as through openings formed through a top section of the front panel portions 662, 663 and 664.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A container for retaining one or more boxes and dispensing medical gloves or other consumables contained in the one or more boxes, comprising:
   a hollow, box holder having an interior cavity for receipt of one or more boxes of consumables, the box holder comprising one or more dispensing openings formed in a front side of the box holder and arranged in spatial communication with the interior cavity, the box holder further comprising an outer surface at a bottom side of the box holder; and
   a movable panel pivotably connected to the box holder and pivotable relative to the box holder between:
   an undeployed condition, in which the movable panel is arranged over the one or more dispensing openings of the box holder and encloses the interior cavity of the box holder, and
   a deployed condition, in which the movable panel is pivoted outward and downward relative to the undeployed condition and is located below the one or more dispensing openings of the box holder, and further in which the movable panel is arranged extending outward of the box holder, with a surface of the movable panel facing upward and providing an area configured to capture one or more consumables fallen out of the interior cavity through the one or more dispensing openings of the box holder, and further in which a bottom end of the movable panel abuts against the entire outer surface at the bottom side of the box holder preventing a further downward rotation of the movable panel.

2. The container of claim 1, wherein the box holder comprises a front panel, a rear panel, a first side panel, a second side panel and a bottom panel, wherein the front, rear, first side, second side and bottom panels define the interior cavity of the box holder, and further wherein the one or more dispensing openings are comprised in the front panel, and the outer surface is comprised in the bottom panel.

3. The container of claim 1, wherein a rear side of the box holder is configured for attachment to a wall.

4. The container of claim 1, wherein the box holder comprises an open top area configured to allow the insertion therethrough of the one or more boxes into the interior cavity of the box holder.

5. The container of claim 1, wherein the movable panel in the deployed condition is arranged forming a 90 degree angle with a vertical plane.

6. The container of claim 1, wherein the movable panel is pivotable relative to the box holder about a rotation axis located at a bottom end of the box holder.

7. The container of claim 1, wherein the movable panel comprises first and second side edges at opposite sides of the surface of the movable panel, the first and second side edges forming a respective angle with the surface such that the first and second side edges retain one or more consumables within the surface of the movable panel when the movable panel is in the deployed configuration.

8. The container of claim 7, wherein the first and second side edges are perpendicular to the surface of the movable panel.

9. The container of claim 1, wherein the box holder comprises one or more elastically flexible flaps extending into the interior cavity of the box holder and configured to adjustably position the one or more boxes of consumables against the front side of the box holder.

10. The container of claim 9, wherein the one or more elastically flexible flaps comprise a plurality of flaps arranged in one or more columns.

11. The container of claim 9, wherein the one or more elastically flexible flaps extend from respective one or more slots formed in the box holder.

12. The container of claim 11, wherein the one or more slots are formed in a rear side of the box holder.

13. The container of claim 12, wherein each dispensing opening of the one or more dispensing openings faces and extends along a respective column of the one or more columns.

* * * * *